United States Patent [19]

Lee et al.

[11] Patent Number: 5,210,117
[45] Date of Patent: May 11, 1993

[54] RESIN COMPOSITION HAVING BIODEGRADABILITY AND HIGH ABSORBENCY, NONWOVEN FABRIC MADE OF THE SAME AND PADS COMPRISING SAID FABRIC

[75] Inventors: Haibang Lee; Soonhong Yuk; Byungchul Shin, all of Daejun-si, Rep. of Korea

[73] Assignee: Korea Research Institute of Chemical Technology, Chungcheongnam-do, Rep. of Korea

[21] Appl. No.: 932,372

[22] Filed: Aug. 19, 1992

Related U.S. Application Data

[62] Division of Ser. No. 675,146, Mar. 26, 1991, Pat. No. 5,166,231.

[30] Foreign Application Priority Data

Mar. 27, 1990 [KR]  Rep. of Korea ............... 90-4118

[51] Int. Cl.$^5$ .................. C08L 5/04; D04H 18/00
[52] U.S. Cl. ........................... 524/28; 428/224; 428/290
[58] Field of Search ................ 428/290; 524/28

[56] References Cited

U.S. PATENT DOCUMENTS 3,554,788  1/1971  Fechillas .................... 428/289

Primary Examiner—Joseph L. Schofer
Assistant Examiner—Wu C. Cheng

[57] ABSTRACT

The present invention relates to a biodegradable and high absorbent resin composition, a nonwoven fabric made of the same and pads comprising this fabric. This resin composition can be prepared by mixing sodium alginate in a predetermined ratio with a synthetic polymer electrolyte. This resin composition can be spun into a fiber and a nonwoven fabric can be made from it. Pads made of this fabric have biodegradability, high absorbency and water retentivity, thereby being applicable for sanitary products.

18 Claims, 4 Drawing Sheets

——○——: Resin composition
——●——: HS-1000
——■——: KR-3050

RESIN COMPOSITION HAVING BIODEGRADABILITY AND HIGH ABSORBENCY, NONWOVEN FABRIC MADE OF THE SAME AND PADS COMPRISING SAID FABRIC

This is a divisional of application Ser. No. 07/675,146, filed on Mar. 26, 1991, now U.S. Pat. No. 5,166,231.

BACKGROUND OF THE INVENTION

(1) Field of the Invention

The present invention relates to a resin composition having biodegradability and high absorbency, a nonwoven fabric made of the same, and pads comprising said fabric. More particularly, the present invention relates to a resin composition which has biodegradability, high absorbency and high water retentivity and can be made into a fiber, thereby being useful in application for sanitary products, and moreover does not cause a pollution problem.

(2) Description of the Prior Art

Generally, a high absorbent material should have 10 times or 1000 times of its own weight in absorbency. Absorbent cotton or pulp has been used for a long time as a high absorbent material. However, said materials have low absorbency, that is, about 20 times of its own weight, and furthermore have poor water retentivity so that the absorbed water therein can be removed easily under the external stress because of absorbing water in the gap of the base material by the capillary phenomenon. Also, said natural absorbent material have too limited production to satisfy the rapidly increasing demand.

Accordingly, as the result of the research of developing material having high absorbency and water retentivity which is synthesized by the artificial synthetic method, polymer a obtained by cross-linking polyvinyl alcohol, polyhydroxyethyl methacrylate, polyethylene glycol and the like was developed in 1965. However, though said polymer has been used as an absorbent resin for soil repairing material in gardening, a viscosity increasing agent of firing water and the medical insemination body and the like, said polymer can not repalce absorbent cotton or pulp because of having low absorbency of only 20-30 times of its own weight, thereby easily removing water therein under external stress.

On July, 1974 the United States Department of Agriculture Research North Laboratory developed a polymer having absorbency of about 1000 times of its own weight. Said polymer is described in detail on page 24 of Chemical Week of Jul. 21, 1974.

After that, several methods of preparing absorbent resin have been suggested as follows:

1) A method of preparing absorbent resin by copolymerization of polyacrylonitrile with starch, as shown in the U.S. Pat. No. 4,769,414;

2) A method of preparing absorbent resin by copolymerization of vinylsaccharide with methacrylic acid and methacrylic acid derivatives, as shown in the EP Patent No. 283,090;

3) A method of preparing high absorbent resin comprising sodium acrylate by using ultraviolet rays or radiochemical method, as shown in the EP Patent No. 287,970;

4) A method of preparing absorbent resin comprising acrylatecopolymer salt by using trimethyl propane triacrylate as cross-linking agent, as shown in the EP Patent No. 312,952;

5) A method of preparing high absorbent resin comprising sodium salt of 2-propeonic acid, acrylic acid, sorbitanol, etc. by using the inverse suspension polymerization method, as shown in the German Patent No. 38 23 729;

6) A method of preparing high absorbent resin by mixing polyacrylate with vinyltrimethoxysilane, as shown in the JP Patent Appln. Laying open No. 06042/1989;

7) A method of preparing absorbent resin by mixing polystyrene with polyacrylate, as shown in the JP Patent Appln. Laying open No. 98657.

However, most of the high absorbent materials prepared by said methods are made of a synthetic polymer which has no biodegradability so that they may cause the serious pollution problem. Also, said high absorbent materials have the poor process efficiency and absorbency in case of the fiber form will be significantly deteriorated as compared with the case of the particle form.

SUMMARY OF THE INVENTION

The present invention seeks to overcome the drawbacks associated with the aforementioned prior art proposals. The object of the present invention is to provide resin composition having biodegradability, high absorbency and water retentivity.

It is further an object of the present invention to provide nonwoven fabric made of said resin composition having excellent absorbency and water retentivity of salt solution and menstrual blood.

It is still further an object of the present invention to provide pads comprising of said nonwoven fabric such as a catamenial pad, diaper, tampon, dustcloth and pad absorbing mother's milk. In order to achieve the above objects, the present invention provides a resin composition comprising sodium alginate and synthetic polymer electrolyte in a certain ratio.

Further objects and advantages of the present invention will be apparent in the following detailed description with reference of the accompanying drawings.

DETAILED DESCRIPTION OF THE INVENTION

Figure 1:
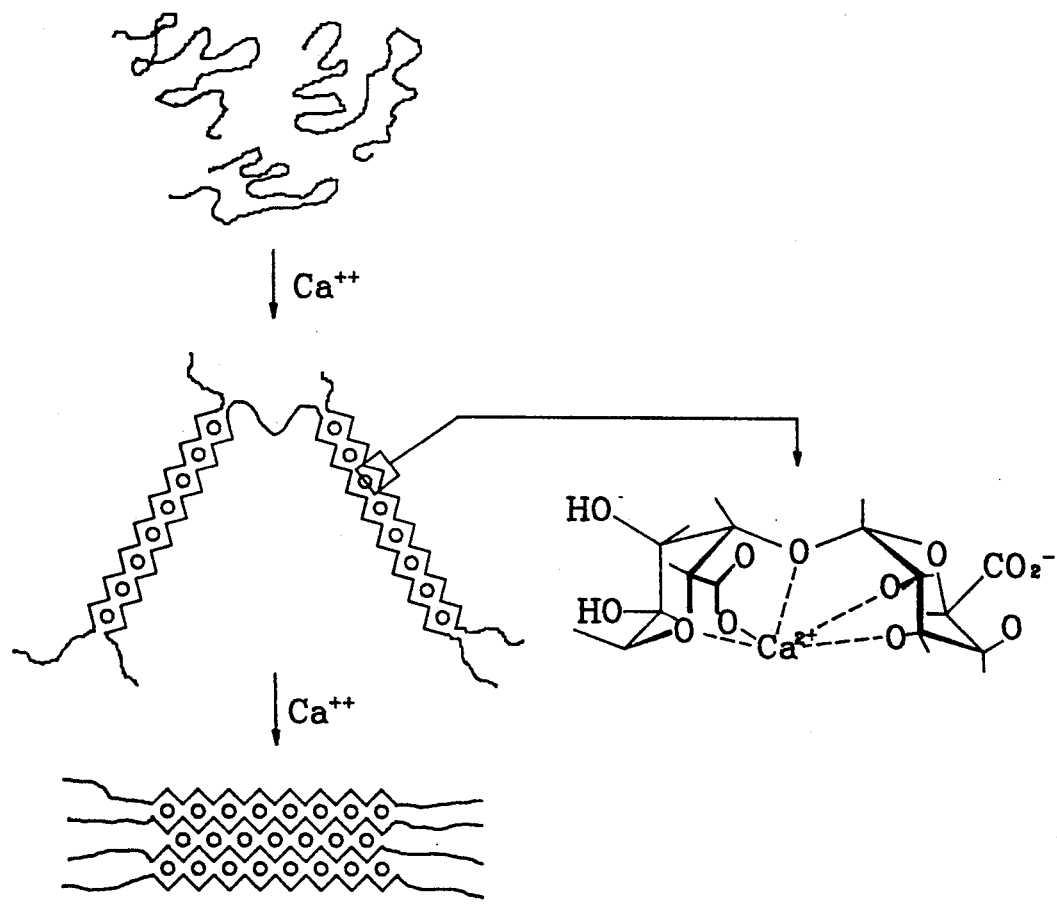
FIG. 1 is an illustration drawing of the reaction mechanism used in the present invention.

One element of resin composition according to the present invention is sodium alginate which has high biodegradability and is a natural polymer of uronic acid polysaccharides. Sodium alginate is contained in large amounts in the giant kelp, a kind of seaweed. The chemical structure of sodium alginate consists of the linear copolymer of D-mannuronic acid and L-guluronic acid at the ratio of 2 to 1.

Meanwhile, the carboxyl group has an ion-exchange ability, thereby having the characteristics of precipitation, dissolution and crosslinking depending upon substitutes. Also, it is possible to use the carboxylated derivatives of sodium alginate, that is, carboxyalkylalginate such as carboxymethylalginate, carboxyethylalginate and carboxypropylalginate (where R is alkyl group having $C_1$-$C_4$) which can be obtained by carboxylating hydroxyl group into carboxyl group instead of or together at a certain ratio with sodium alginate. The preferred methods of carboxylification of alginate is described in the Korean Patent Appln. Nos. 88-8832, 88-16096 and 88-16160, and the U.S. patent application Ser. Nos. 07/379,012 and 07/445,186.

One of the preferred methods of obtaining carboxylated alginate in said applications is to prepare alkalified alginate treating hydroxyl group in alginate with sodium hydroxide (NaOH), and thereby to obtain carboxylated alginate by adding halogenated carboxylic acid such as chloroacetic acid to the solution of alkalified alginate. A halogenated carboxylic acid used in the present invention is a compound having $C_1$-$C_4$ such as chloroacetic acid, chloropropionic acid, $\alpha$-chlorobutyric acid, $\beta$-chlorobutyric acid and $\gamma$-chlorobutyric acid and the like.

The carboxylated derivatives of sodium alginate obtained by the above method contain 2-3 times the amount of carboxyl group as much as that of alginate. The degree of esterification representing the amount of carboxyl group is 0.6 in case of alginate and is 1.2-2.5 in case of carboxylated alginate. Also, the absorbing speed and the mechanical properties of the same can be increased. The reaction formula of synthesis of carboxylated alginate can be shown as follows:

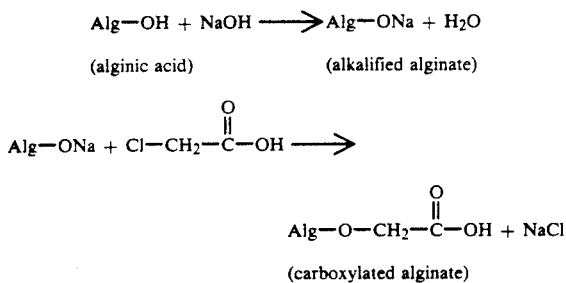

Sodium alginate is widely used for food, pharmacy, cosmetics medical treatment, chemical industries and the like. The cost of these materials is very cheap and said materials are not toxic and antigenic against a living body. Especially, they are very compatible with the living body.

Meanwhile, another element of resin composition according to the present invention is a synthetic polymer electrolyte. Said synthetic polymer electrolyte is to improve absorbency, water retentivity and the gel strength of resin composition. Absorbency of said materials depends on the ion concentration of the same. Accordingly, synthetic polymer electrolyte used preferably in the present invention is a composition which is able to increase ion concentration thereof.

Generally, synthesized polymer electrolyte can be classified into two types. One type is acidic polymer electrolyte having carboxyl group, sulfonic group, phosphoric group or nitric group as a functional group in the polymer backbone such as polyacrylamido2-methyl-1-propane sulfonic acid, polystylene sulfonic acid or polymethyl methacrylic acid. The other type is a basic polymer electrolyte having amine group or imine group as a functional group in the polymer backbone such as polyethyleneimine, polyacrylamide, polyaminoethyl methacrylate or the derivatives of polyaminoethyl methacrylate. Said synthetic polymer electrolytes are commercially available on the market and processed into various products such as adhesives, paints, fibers, cosmetics, shampoo, dentifrice and the like.

Accordingly, the inventors of the present invention use the advantages of said sodium alginate and said synthetic polymer electrolyte in order to develop resin composition having biodegradability and high absorbency. Since said sodium alginate has high biodegradability and said synthetic polymer electrolyte is also water-soluble, sanitary products comprising said resin composition may not cause the pollution problem and is suitable for a catamenial pad, diaper, tampon, pad absorbing mother's milk dustcloth and the like.

Furthermore, said resin composition has the good process efficiency, thereby being processed easily into the fiber form. Generally, resin composition in the fiber form shows the decreased absorbency and water retentivity as compared with resin composition in the particle form. However, said resin composition does not show such decreased absorbency and water retentivity even when it is processed into the fiber form.

In the present invention, it is preferable that resin composition contains 20-99% by weight of sodium alginate with respect to the total amount of resin composition. If the amount of sodium alginate is less than 20% by weight, resin composition may contain so much synthetic polymer electrolyte that the fiber spinning is difficult. If the amount of sodium alginate is more than 99% by weight, resin composition may contain so little synthetic polymer electrolyte that the gel strength and absorbency thereof may get deteriorated.

Meanwhile, the resin composition according to the present invention is obtained through the reaction mechanism shown in FIG. 1, which in polyacrylic acid is used as a synthetic polymer electrolyte.

Through the mechanism, it is known that sodium alginate is formed into insoluble gel (calcium alginate network) via an egg-crate complex formation with $Ca^{2+}$ ion as described in the Journal of Carbohydrate Research, 66 145(1978). $Ca^{2+}$ ion can be replaced by $Al^{+3}$ ion in the above mechanism.

Figure 2:
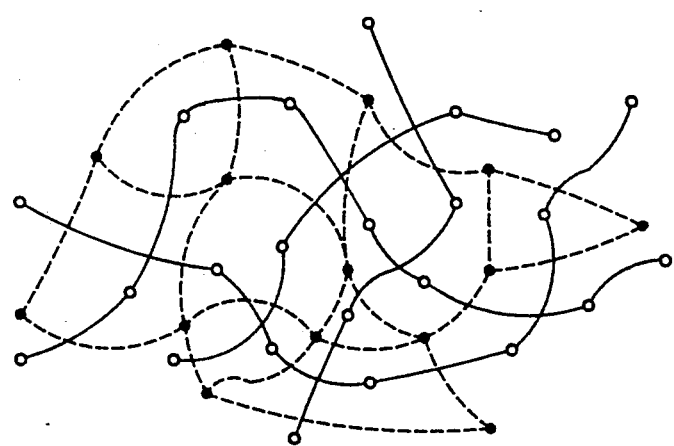
FIG. 2 is an illustration drawing of composition obtained through the above reaction mechanism.

The above mechanism can be applied for the resin composition according to the present invention which comprises sodium alginate and polyacrylic acid, thereby being able to form the composition as shown in FIG. 2.

In FIG. 2, "●---●" represents the crosslinked network of calcium alginate and "O——O" represents polyacrylic acid. As shown in FIG. 2, polyacrylic acid can not diffuse through the calcium alignate network because of heavy molecular weight thereof.

The resin composition according to the present invention prepared via the reaction mechanism can be spun into the fiber by the known spinning machine. During the spinning process, the calcium alginate network is formed via an egg-crate complex formation, whereby sodium alginate and polyacrylic acid form the interpenetrating system(IPNs).

Also, the present invention provides nonwoven fabric having biodegradability and high absorbency, and pads comprising said fabric. Said nonwoven fabric made of the fiber comprising said resin composition is obtained by the needle punching machine, and washed off with a predetermined washing solution. The recipe for washing the solution was described in detail in the following examples.

Now, the preferred embodiments of the present invention will be described as follows.

Examples 1-8 and comparison examples 1-2 are discussed below.

After dissolving sodium alginate and polyacrylic acid in different ratios as shown in Table 1 in the distilled water in order to prepare 1% solution thereof, the solution was spun into the fiber by a wet spinning process.

Spinning conditions are as follows:

| | |
|---|---|
| Spinning pressure: | 0.5-1.0 kgf/cm² |
| Spinning speed: | 5-8 m/min. |
| L/D of spinning nozzle: | 110 |
| Diameter of nozzle: | 100 μm φ |
| Coagulating bath: | Coagulating solution containing CaCl2 was circulated continuously |
| Ratio of drawing: | 1-2 |

The nonwoven fabric was made with the obtained fiber by the needle punching machine. In addition, a washing solution was prepared from the mixture of 100 g of ethanol, 400 g of water, and 50 g of sodium acetate and used to control the number of Ca2+ cross-linkage. Ca²⁺ cross-linkage in the fabric was washed off, thereby leaving only minium Ca²⁺ cross-linkage which is able to maintain IPNs in order to increase the concentration of carboxyl group which plays a major role in exhibiting the high absorbency.

After pouring the washing solution on the nonwoven fabrics prepared according to these examples, in the amount of 30 times of the fabric weight the fabric became wet completly and then left at 40° C. for 30 minutes. After that the fabric was tilted at 45 degrees for 30 minutes to get rid of the washing solution. After that, 50% ethanol solution with the amount of 100 times of the weight of the fabric was poured on the fabric, thereby washing off the unreacted washing solution from the fabric. The fabric was dried at 60° C. for 20 minutes, and pads were made of the fabric.

In order to compare the efficiency of the pads prepared according to the present invention as in examples 1-8 with the comparison examples, several tests were carried out.

Test 1 is a water absorbency and saline water absorbency test.

The water absorbency and the saline water absorbency were tested by the Tea-bag method, and the results thereof are shown in Table 1.

According to Table 1, it is apparent that the pads containing resin composition according to the present invention has much higher water absorbency and saline water absorbency than pads containing only synthetic polymer electrolyte such as polyacrylic acid.

TABLE 1

| Example No. | Composition ratio of sodium alginate/ polyacrylic acid (% by weight) | Amount of water absorption (g/g) | Absorbing amount of 0.9% NaCl aqueous solution (g/g) |
|---|---|---|---|
| Comparative example 1 | 100/0 | 80 | 25 |
| Example 1 | 99/1 | 110 | 42 |
| Example 2 | 90/10 | 250 | 62 |
| Example 3 | 85/15 | 290 | 67 |
| Example 4 | 80/20 | 350 | 70 |
| Example 5 | 70/30 | 400 | 73 |
| Example 6 | 50/50 | 400 | 75 |

TABLE 1-continued

| Example No. | Composition ratio of sodium alginate/ polyacrylic acid (% by weight) | Amount of water absorption (g/g) | Absorbing amount of 0.9% NaCl aqueous solution (g/g) |
|---|---|---|---|
| Example 7 | 30/70 | 400 | 75 |
| Example 8 | 20/80 | 400 | 75 |
| Comparative example 2 | 0/100 | 180 | 45 |

Test 2 is a absorbing speed test.

Figure 3:
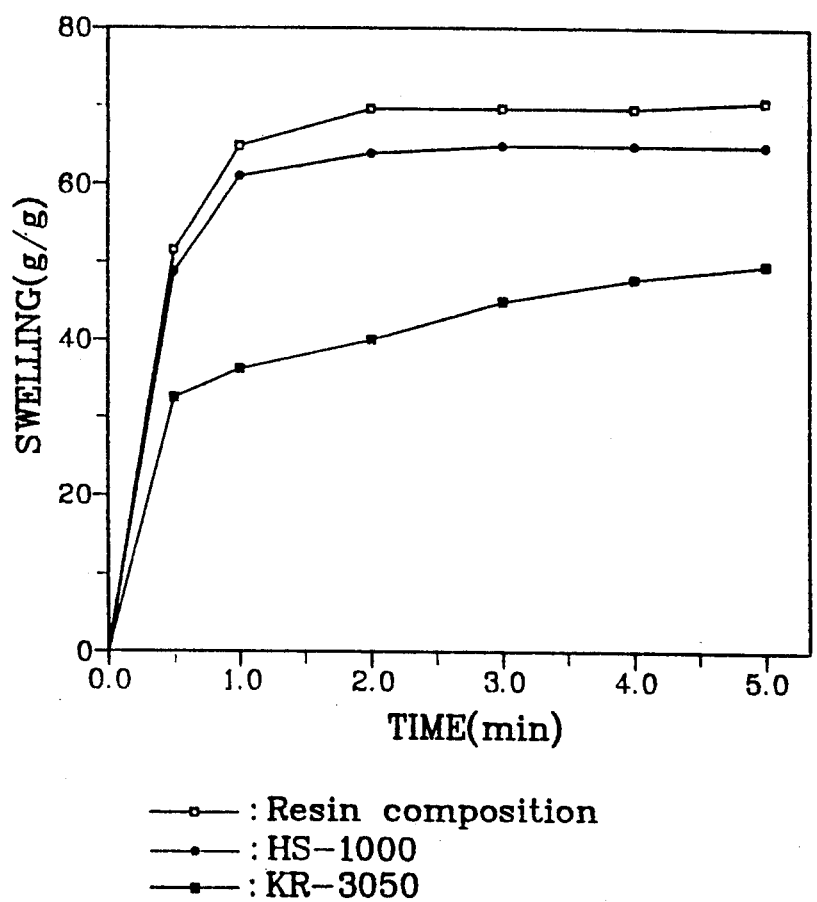
FIG. 3 is a graphical illustration drawing showing the absorbing speed of pads.

Absorbing speed test of pads were carried out, and the results thereof are shown in FIG. 3.

In this test, a pad made of resin composition according to example 4 was used as a representation of the present invention while commercial products made of the fiber containing carboxymethyl alginate described in the Korean Patent Appln. No. 88-16096, (Commercial name: "KR-3050") and commercially available products in Korea under the trademark of "HS-1000" from Songwon Ind. were used as the representation of the reference.

Since the absorbent material used for sanitary products such as diaper, catamenial pad, tampon, dustcloth, pad absorbing mother's milk and the like is subjecting under the saline condition, the absorbing speed test was carried out using 0.9% NaCl solution.

Generally, resin composition has higher absorbing speed in the particle form than in the fiber form because the absorbing speed depends upon the surface area of the material. However, composition in the particle form has poor dispersiveness, thereby is inconvenient for handling. Accordingly, though the composition in the fiber form has a lower absorbing speed, the resin composition according to the present invention was prepared in the fiber form.

As it is apparent in FIG. 3, the pad according to the present invention has superior absorbency as showing a swelling of more than 80% of equilibrium state (maximum swelling: 70 g/g) within 30 seconds, and also the maximum swelling thereof much higher than that of HS-1000 and KR-3050.

Test 3 illustrates the variation of the absorbing speed depending upon the change of concentration of saline solution.

Figure 4:
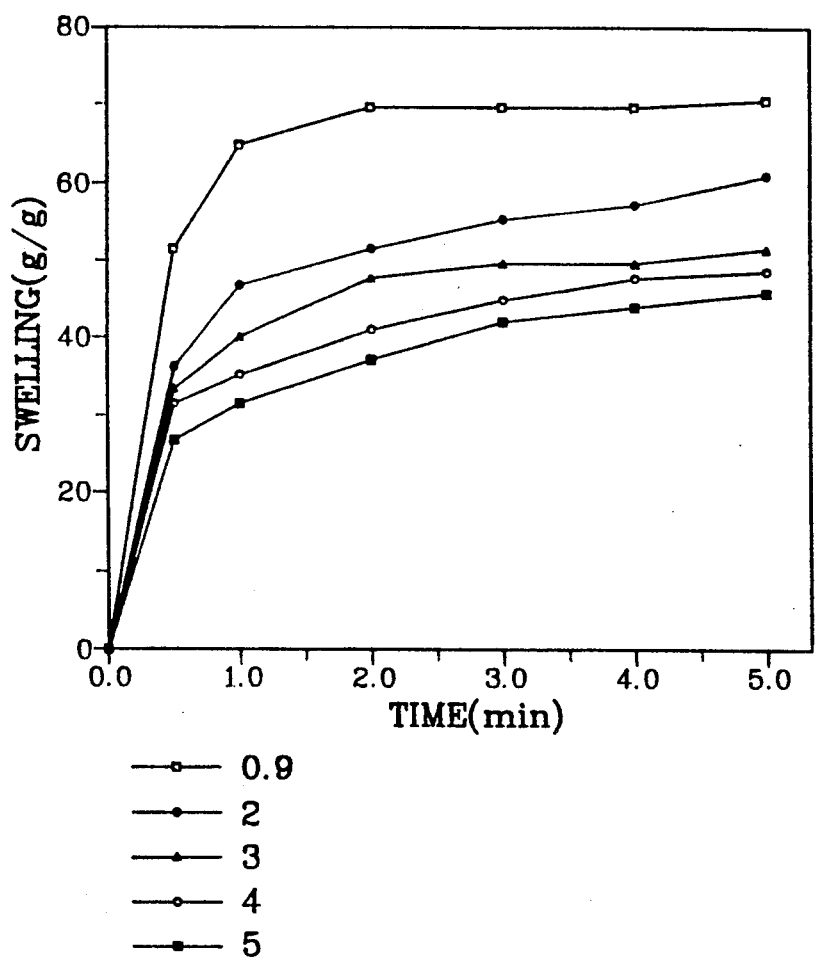
FIG. 4 is a graphical illustration drawing showing the variation of the absorbing speed depending upon the change of concentration of saline solution.

Generally, the absorbent materials on the markets may bring out the decrease of absorbency and the absorbing speed proportional to the increase of the concentration of saline solution. FIG. 4 shows the decreased absorbency of pad according to the present invention depending upon the change of concentration of saline solution.

Test 4 is a water retentivity test.

The water retentivity of the pad according to the present invention was measured by the centrifugation method. The results thereof are shown in Table 2. As apparent in table 2, said pad has the reasonable water retentivity as compared with commercial products as HS-1000 which has no biodegradability, while pad has superior biodegradability and high absorbency comprising natural substances.

TABLE 2

| Rotation number (rpm) | Water leakage ratio (%) | | |
|---|---|---|---|
| | KR-3050 | Resin composition | HS-1000 |
| 800 | 4.9 | 2.7 | 0 |
| 1200 | 15.4 | 10.1 | 7.5 |

TABLE 2-continued

| Rotation number (rpm) | Water leakage ratio (%) | | |
|---|---|---|---|
| | KR-3050 | Resin composition | HS-1000 |
| 1400 | 17.1 | 12.9 | 9.0 |

What is claimed is:

1. A nonwoven fabric prepared by the process comprising the steps of:
   spinning resin composition comprising sodium alginate and a synthetic polymer electrolyte in a ratio of 20:80 to 99:1;
   making the fiber obtained thereby into a nonwoven fabric; and,
   washing said fabric with a washing solution.

2. A nonwoven fabric as claimed in claim 1, wherein said synthetic polymer electrolyte is an acidic polymer electrolyte selected from the group consisting of a polyacrylic acid, polyacrylic acid sodium salt, polyacrylamido-2-methyl-1-propane sulfonic acid, polyethylene sulfonic acid and polymethyl methacrylic acid.

3. The nonwoven fabric as claimed in claim 1, wherein said synthetic polymer electrolyte is a basic polymer electrolyte selected from the group consisting of polyethyleneimin, polyaminoethyl methacrylate and its derivatives and polyacrylamide.

4. A catamenial pad comprising the fabric as claimed in claim 1.

5. A catamenial pad comprising the fabric as claimed in claim 2.

6. A catamenial pad comprising the fabric as claimed in claim 3.

7. A diaper comprising the fabric as claimed in claim 1.

8. A diaper comprising the fabric as claimed in claim 2.

9. A diaper comprising the fabric as claimed in claim 3.

10. A tampon comprising the fabric as claimed in claim 1.

11. A tampon comprising the fabric as claimed in claim 2.

12. A tampon comprising the fabric as claimed in claim 3.

13. A pad absorbing mother's milk comprising the fabric as claimed in claim 1.

14. A pad absorbing mother's milk comprising the fabric as claimed in claim 2.

15. A pad absorbing mother's milk comprising the fabric as claimed in claim 3.

16. A dustcloth comprising the fabric as claimed in claim 1.

17. A dustcloth comprising the fabric as claimed in claim 2.

18. A dustcloth comprising the fabric as claimed in claim 3.

* * * * *